United States Patent

Snyders

Patent Number: 6,095,968
Date of Patent: Aug. 1, 2000

[54] REINFORCEMENT DEVICE

[75] Inventor: Robert V. Snyders, Ballwin, Mo.

[73] Assignee: Cardio Technologies, Inc., Pine Brook, N.J.

[21] Appl. No.: 09/288,488

[22] Filed: Apr. 8, 1999

Related U.S. Application Data

[60] Provisional application No. 60/081,286, Apr. 10, 1998.

[51] Int. Cl.[7] ................................................. A61M 1/12
[52] U.S. Cl. ................................................................ 600/16
[58] Field of Search ................................. 600/16, 17, 18, 600/37; 623/1, 3; 601/153

[56] References Cited

U.S. PATENT DOCUMENTS

| | | |
|---|---|---|
| 4,690,134 | 9/1987 | Snyders . |
| 5,169,381 | 12/1992 | Snyders . |
| 5,256,132 | 10/1993 | Snyders . |
| 5,558,617 | 9/1996 | Heilman et al. ........................... 600/16 |
| 5,702,343 | 12/1997 | Alferness ................................... 600/37 |
| 5,800,528 | 9/1998 | Lederman et al. .......................... 623/3 |
| 5,910,124 | 7/1999 | Rubin ....................................... 601/153 |

*Primary Examiner*—George Manuel
*Attorney, Agent, or Firm*—Darby & Darby

[57] ABSTRACT

A heart assist device intended for the long term support of certain late-stage cardiac failure states, particularly those known in the practice of cardiology to be called a dilated cardiomyopathy. A method is described wherein a "viscous cardioplasty jacket" is fashioned to provide a buttressing effect to the ventricular heart walls to thus render a more efficient cardiac contractile mechanism whereby the patient is afforded improved heart function to allow increased physical activities. Such a viscous compliant enclosure of the ventricular heart masses can be utilized concurrently with recognized drug therapy which is sometime lacking in beneficial effect for these patients and is far less traumatic than the currently practiced surgical cardiomyoplasty (CMP) procedure. Application of this device may be accomplished through a relatively non-invasive endoscopic procedure in a more refined methodology of anatomical implantation of the device.

12 Claims, 2 Drawing Sheets

REINFORCEMENT DEVICE

CROSS-REFERENCE TO RELATED APPLICATIONS

Provisional Application filed Apr. 10, 1998, Ser. No. 60/081,286

BACKGROUND OF THE INVENTION

This invention very simply constitutes a modification of use with minimal fabrication changes of the original device as defined in U.S. Pat. No. 5,256,132 (Snyders) which invention is designed for acute heart failure support via a cyclical pneumatic ventricular compression in timed synchrony with the ambient heart rhythm. The present methodology pertains to the provision of long-term support for individuals suffering from certain late-stage heart failure disease entities as are particularly known in medical practice as the dilated cardiomyopathies. These disease states are of frequent occurrence and carry a high mortality rate if not corrected in a reasonable period of time. This modification consists of the instillation of a high viscosity silicone (or other) fluid into the encircling retention sac space of the previously described device (U.S. Pat. No. 5,256,132) to enclose the heart ventricles, with a resultant reduction in ventricular systolic and diastolic volumes of the heart. Such volume reductions are known to reduce myocardial oxygenation requirements for any given level of cardiac contractility needed for ongoing adequate cardiac functional requirements for any given level of physical activity by the patient. Such a modification and application of the previously described VAD (Ventricular Assist Device), though minimally changed in its original fabrication, could open a new area of interventional long-term support for those patients afflicted with a dilated cardiomyopathy.

The VAD jacket is quite easily adjustable to any cardiac size and is virtually self-sizing relative to circumferential dimension requirements even for the very largest hearts because of the diminutive fabrication features of the device for insertion around the heart and inside the pericardial sac, which location is its appropriate compliant anatomical site of implantation. Subsequent filling of the sac space with a viscous silicone or other equivalent non-compressible fluid through the fill line of the device to enclose the ventricular masses with either no or minimal pressurization therein as registered in a sac pressure monitor line then results in a viscous cardioplasty reinforcement of the thinned ventricular walls with a resultant reduction in LV (Left Ventricular) and RV (Right Ventricular) diameters to effect a desirable reduction of wall stress. This procedure thus effectively provides for a "reverse remodeling" of the heart via both a diastolic and systolic volumetric restriction but not constriction of the ventricular anatomy and with a subsequent improved physiological benefit to cardiac function.

The Law of LaPlace defines that this physiological benefit is sequential to reduced wall stress (wall tension) consequent upon the reduction in chamber diameter and increased chamber wall thickness provided by such a girdling "cardioplasty" event, and such an alteration results in reduced myocardial oxygen needs sequential to that reduction in wall stress. Such reduced oxygen needs at rest then convert to increased myocardial oxygen availability for increased physical activity and a resultant improved functional class for the patient. It will be noted below that an important provision of a high viscosity fluid (e.g. to 12,500 ctsk.) for sac filling is suggested for use because of the increased inertial character of those higher viscosity fluids such that areas of ventricular akinesia or dyskinesia subject to paradoxical wall motion in systole should be somewhat restrained from such an undesirable dysfunctional event with the ventricular wall enclosure as proposed. Such restraint would provide a beneficial improvement in systolic ejection volumes and thus be additive to the beneficial girdling restraint derived from the cardioplasty jacket application itself.

BRIEF SUMMARY OF THE INVENTION

The basic fabrication components of the device are essentially quite similar to those described in U.S. Pat. Nos. 4,690,134 (Snyders), 5,169,381 (Snyders) and 5,256,132 (Snyders) with those important features comprising 1) a thin (2 mm.) flexible but inelastic dacron reinforced external visible shell wall; 2) a series of Nitenol alloy shape-memory strips (15 by 30 mils) laminated within that shell wall to develop an "open" conformation for the device in its functional position around the heart; 3) an internal flexible compression sac (two in the original pneumatic device, but now formed as a unitary sac in the cardioplasty device) to receive a viscous fill liquid in the modified cardioplasty device, with sac caliber being about 10 to 15 mils; 4) an adjustable anterior wedge closure element to facilitate circumferential fitting needs of the device; 5) an upper soft non-inflating collar for a protective presentation of the device to the major vessels accessing the heart from above and behind; 6) a primary accessing conduit line entering the inferior apex extremity of the VAD which served as the gas transit shuttle line in the prior device but now will serve as the viscous fluid fill line for the cardioplasty jacket; and 7) a single sac pressure monitor line (rather than the paired monitor lines for the two sac spaces in the original device) for pressure readings from the viscous liquid fill element contained within the compression sac space.

The presently singular unitized flexible sac of the cardioplasty device (now a low-grade compression sac) will then quite completely envelop the right and left ventricular heart masses when such sac space is filled with a high viscosity silicone or other similar biocompatible liquid after implantation around the heart in an endopericardial location. The small wedge closure adjusting curtain, though not apportioned any liquid filling component unto itself, will nonetheless cooperate in the compressive envelopment process because of the essentially uniform distribution of physical forces throughout the entire heart-contacting elements of the flexible sac liner because of the continuity of the liner with the wedge closure curtain at all of their adjacent margins. The free-flow physical character of the viscous fluid component will allow an equilibrating distribution of such a fluidic compressive force across both the R (right) and L (left) ventricular epicardial surfaces as transferred through the responsive flexible sac liner via this planned viscous cardioplasty ("reshaping" of the heart) interventional event.

The technique of insertion of the cardioplasty jacket around the heart may be done via an "open" surgical procedure, such as a sternotomy or a thoracotomy, but it is understood that the device may be inserted through an endoscopic procedure with the use of appropriate endoscopes, endoscopic instrumentation, light source, accessing ports, and a probable single-lung anesthesia event to allow of left chest accessing to the pericardial and cardiac structures. The device in its wrapped or folded configuration can then be passed through a suitable introducer cannula as pertains with the original pneumatic VAD, and can access the endo-pericardial anatomical implantation site either via a trans-thoracic intercostal, a trans-diaphragmatic subcostal, or via the trans-xiphoid route. Regardless of the selected implantation method, the device can then be stabilized in its endopericardial location via suture attachment of the device to the adjacent pericardial sac at various optional locations. Because of the diminutive features of the implanted VAD structural dimensions the pericardium can be saved in its totality, and such saving with an ideally congruent "fit" of the device within the pericardial sac allows of a free choice of suture or, if desired, staple fixation attachment sites of the VAD to the pericardial sac at various optional locations. This attachment site may be at the VAD jacket apex junction with the fill line conduit via device approximation hereof to the adjoining pericardial-diaphragmatic aggregate, or along the upper suturable collar of the VAD jacket to the adjacent pericardium, or at various other locations on the VAD wall due to the reinforced woven dacron composition of the outer shell wall having suturable capabilities. It is also understood that because this modification of VAD application results in an essentially static device devoid of the displacing forces incident to rapidly fluctuating pressure events incurred with the pneumatic device, then such a state of its essentially static environment in its implanted mode would require a minimum of stabilizing measures.

All fabrication materials will be of biocompatible medical-grade elastomers of either silicone or polyurethane polymeric nature or other copolymers or other equivalent biocompatible elastomeric substrate materials. In addition, it should be noted that most silicone fill fluids contemplated for use have a specific gravity of 0.97 or 0.98 which is quite ideal for this application. The cardioplasty fill fluid will be of any compatible polydimethylsilicon or fluoropropylsilicone or other equivalent high-viscosity fluid of similar density. An added enhancement of this embodiment may be the use of a fluid reservoir from which to fill the cardioplasty jacket sac space. Such a fluid reservoir would likewise be of a bio-compatible material and could be left implanted in the upper abdominal subcutaneous space for a subsequent re-filling of the sac if desired, or simply removed and held in reserve for such a future use. Likewise, the device could simply be filled by any type standard syringing procedure from an external viscous fluid container source with the process discontinued after appropriate filling and the accessing end of the VAD fill line clamped off or simply plugged and then left embedded in an abdominal subcutaneous site for revisiting if deemed necessary. Such a future revisiting of the fill line conduit for viscous fluid volume or pressure adjustments could quite reasonably be performed under local anesthesia following retrieval of the conduit from a superficially placed subcutaneous site. The outer external terminus of the pressure monitor line may also be eventually transplanted to a convenient subcutaneous location after a reasonable time for immediate post-insertion documentation of satisfactory VAD function. This line would be obviously preserved for future accessing and pressure monitoring needs, and as with the fill line, such could be accomplished with local anesthesia. Any protracted externalization of either the fill line or the monitor line would be discouraged due to obvious known infectious events that may result thereupon.

Because of the expected long-term application of the viscous cardioplasty jacket it is understood that there will be some increased opportunity for either friction-induced epicardial inflammatory responses or migrant silicate-induced or other elastomer-induced reactive tissue responses to occur. Therefore, in anticipation of such events it is considered reasonable that some type steroid dispersion within the elastomeric substrates of the device may be performed, and additionally the use of some of the known available agents to provide a friction-reducing coating, particularly for the heart-contacting surface of the flexible compression sac liner, will be the subject of a studied undertaking of that potential adversity.

The question of the appropriate level of sac pressurization after viscous fluid filling of the sac space will best be determined by experimental in vivo evaluations of such developed pressures during the filling process. There may be sufficiently effective benefits from gravity sac filling for sufficient reduction of ventricular volumes without the necessity of any pressure development being required in the enclosing sac spaces. Such evidencing would follow appropriate echocardiographic and volume conductance catheter evaluations of the resultant cardiac structural remodeling both concurrent with the viscous fluid filling process as well as with serial follow-up evaluations of those known significant parameters of improved cardiac anatomical alteration known to reduce wall stress. With additional in vivo analysis it may be found that some minimal pressurization is beneficial for attaining the desire effect, though lesser pressures in the range of 2 to 10 mm Hg are contemplated for this projected benefit. Such an essential monitoring of these numbers is performed through the indicated sac pressure monitor line and can be instantly read on some style of a simple "bedside" aneroid manometer or with the use of a more refined pressure transducer. Quite obviously, excessive pressurization of the system must be avoided lest frank cardiac tamponade occur following excessive filing of the sac space.

DETAILED DESCRIPTION OF THE INVENTION

Figure 1:
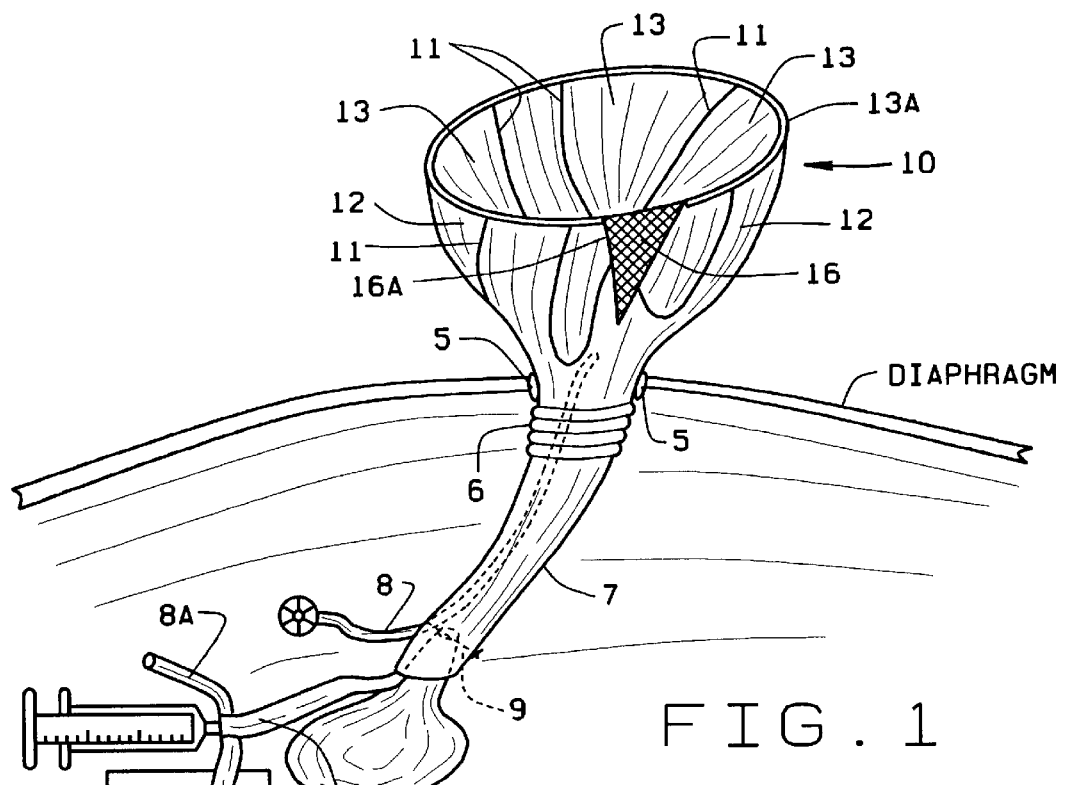
FIG. 1 is a perspective frontal (anterior) view of the stented cardioplasty jacket showing possible sourcing of the viscous fluid supply for flexible sac filling.

Referring to FIG. 1, the cardioplasty jacket outer shell wall of the device 10 that is stented at 11 is composed of a dacron (or equivalent fiber) woven flexible but inelastic elastomeric biocompatible material 12 and presents itself as the visible external VAD element. The sac space membrane 13 is a thin flexible and elastic elastomeric sheath which envelops and abuts the ventricular heart masses and is securely bonded by its margins to the internal aspect of the shell wall 10 in all of its peripheral dimensions. It is within the sac space so created between the inelastic outer shell wall 12 and this inner sac lining 13 that the viscous fluid component of the functional jacket is contained and by which with either no or minimal pressure development of that contained fluid that a reinforcement effect is generated over the right ventricular wall 14R and the left wall 14L of the free walls of the heart (See FIG. 5). The shape-memory stents 11 are orientated in a looping type encirclement of the VAD to provide a conformational geometry to the device 10 in its operational state, and such stenting means 11 likewise effects a "blooming" event for the VAD when the device 10 is implanted using an endoscopic procedure means 15 of FIG. 4 for its insertion around the heart. The wedge closure adjustment curtain 16 serves as a means of obtaining the most appropriate circumferential fit of the VAD jacket 10 to the heart and is fashioned of a thin (5 to 10 mil, or about ⅛ or ¼ mm caliber) dacron knit flexible and sutureable biocompatible elastomeric material that can be pleated unto itself after VAD application to enhance the proper fitting of the device 10 to ambient heart size.

This V-shaped wedge closure curtain 16 is securely bonded at its margins to the adjoining external inelastic shell margins 12, and thus together they effectively provide an inelastic though flexible outer shell wall against which the viscous fluid content of the enclosing unitized sac space can produce a reinforcement type buttressing effect through the pliable inner sac liner against 13 the right R14 and left L14 free ventricular walls for the desired benefit to heart function. Element 5 in FIG. 1 is a thickened narrow wrap of dacron sheeting to provide a suture "tab" for possible stabilization of the VAD at its apex to the adjacent pericardio-diaphragmatic aggregate, if such be desired by the implantation surgical team. The flexible neck element 6 is an added provision of an approximately 2 cm. length of elastomer dispersion-sealed arterial woven tubular graft to allow rotation of the viscous fluid fill line 7 to various selected positions of exit of that line from the VAD implantation site. The choice of exit site would include passage of the conduit fill line 7 either through a sub-costal transdiaphragmatic route, though a trans-thoracic intercostal space, or possibly via the trans-xiphoid route, any of which routings would be a surgical team judgmental decision. The somewhat rigid conduit fill line 7 will be about 12 to 14 mm. diameter, fabricated of a silicone or other equivalent biocompatible medical grade elastomer, and will be filled from any of a variety of viscous fluid sources, such as for example a simple bulb syringing vessel, 7A, or a calibrated standard Luer-Lock syringe with a 3-way adapter for more controlled fluid filling end which fits into a valved device 7B at the inlet end of tube 7, or the filling procedure can be accomplished from an implantable flexible reservoir 8, not unlike that style utilized for breast implant purposes, with the use of some type adapter connector 9 at the fill line external port. The viscous fluid fill line 7 extends up to the VAD apex through the flexible neck element 6 with which it is securely bonded, and then leads to the interior of the sac space compartment to thus "charge" that space with the viscous fluid element after a preceding appropriate fitting of the device around the heart.

The silicone fill fluid must be essentially all liquid and free of gas to avoid any sac space occupancy by air which being compressible would defeat the necessarily incompressible and inertial character of the viscous fill fluid needed for reinforcement effect. A pre-insertional filling of the sac spaces and the fill line 7 to displace trapped air with a subsequent controlled emptying of the viscous fluid from recesses in the sac space has proven sufficient thus far to control such air trapping events. Other methods of air venting from the system can be accomplished by using 1-way valves (as utilized for breast implant fill procedures), with the reservoir 7C or via an air vent line adaptation with a 3-way stopcock as in 7B.

Insofar as there must be some documentation of developed sac space viscous fluid pressures with use of this device, there is incorporated a pressure monitor line of suitable biocompatible elastomeric material 8A, which transits through the fill line from an externalized site and leads into the lower fluidic sac space for reading that pressure development as sac filling progresses. As noted above, either fairly low pressures may be desired (2 to 10 mm Hg.), or possibly no pressurization of the sac space fluid component may have to be generated to produce the desired remodeling and reinforcement effects. These latter have been indicated previously to comprise reduced ventricular diameters as per echocardiographic study and with concomitant ventricular volume reductions via conductance catheter analysis. Various or other recognized parameters of improved cardiac functional status and cardiac reserve are well known in the practice of clinical cardiology and the analysis of such may also be utilized. The specific sac pressure readings may be concurrently evidenced with the use of some type simple "bedside" aneroid manometer 8A (not shown, or a more refined pressure transducer may be used particularly during the initial acute fluid filling phase of the device.

Figure 2:
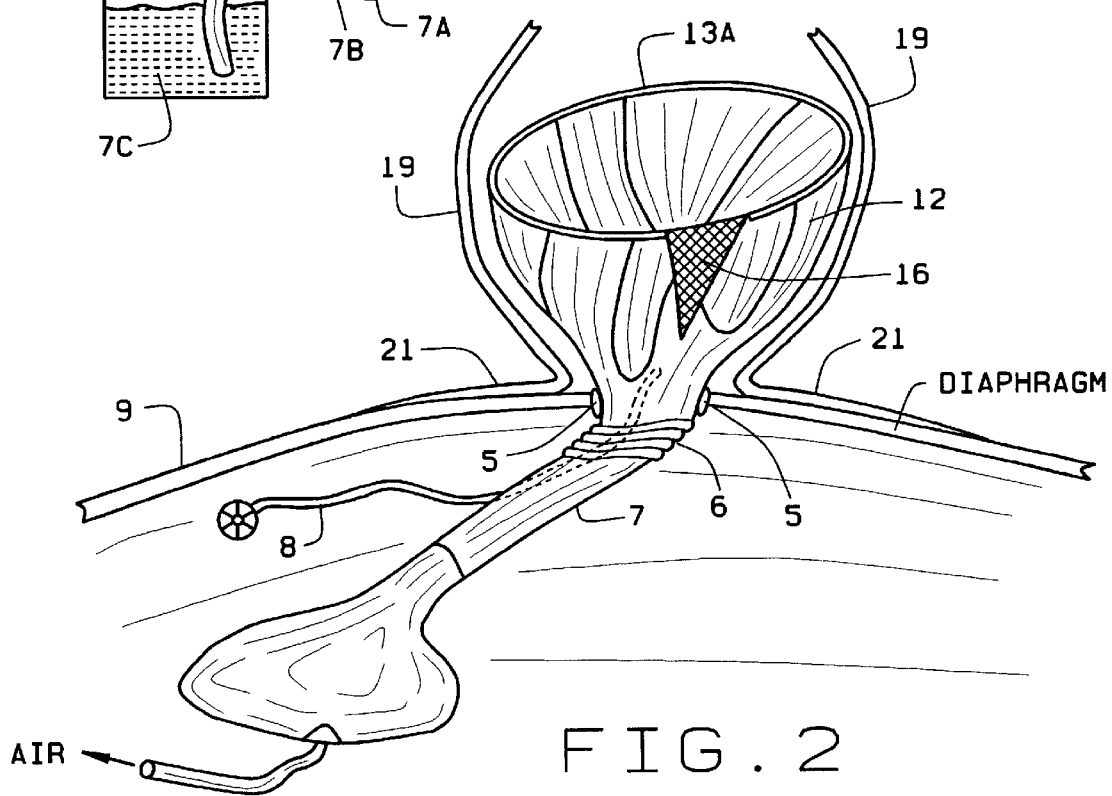
FIG. 2 is the same frontal view showing the important congruent fitting of the jacket device within the endopericardial space with total saving of the pericardial sac to ensure device stability. A biocompatible collapsible viscous fluid reservoir (possibly implanted) is also shown.

Relating to the pericardial sac 19 as demonstrated in FIG. 2 it is understood that the dimensional character of the VAD cardioplasty jacket is such that the device can be implanted into its functional endo-pericardial location with total preservation of this structure. An anterior percardiotomy is required for open insertion of the VAD jacket following either a sternotomy or thoracotomy procedure, but the diminutive size of the device together with the known acceptance of the somewhat distensible pericardial sac of the volumetric needs for the device, make it the ideal vessel for implantation into this important anatomical site without impaction on either the cardiac or pericardial sac anatomical or physiological integrity. The anterior cardiotomy can be approximated (via sutures or staples) in normal continuity after device insertion, and in fact this salvage of the pericardial sac conserves it as the ideal retainment bed for the VAD. The same features of idealized fitting and congruent spatial relationships between the implanted device and the receiving pericardial sac will likewise pertain if the device ise inserted through an endoscopic procedure.

Figure 3:
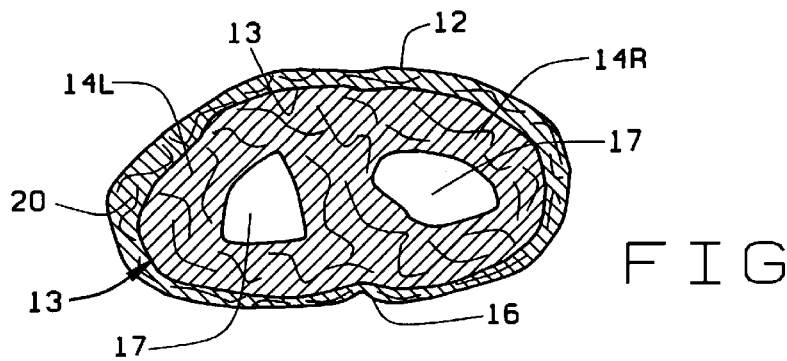
FIG. 3 is a cross-sectional view at the mid-ventricular "waist" of the heart, with enclosure of the entire epicardial heart surfaces by the compression sac filled with viscous fluid component.

FIG. 3 shows a cross-sectional view of the VAD jacket at the mid-ventricular or "waist" level of the heart. Item 14R and 14L represents myocardial heart substance and item 17 represents their respective ventricular cavities. Item 20 represents the viscous fluid component within the enclosing sac space and 13 shows the flexible sac liner intimately applied to the epicardial ventricular heart surfaces. Item 16 is the anterior wedge closure site depicted in an "indenting" fashion, but not factually indenting the cardiac substance because of its integral continuity with the external dacron reinforced shell wall of the device 10.

Figure 4:
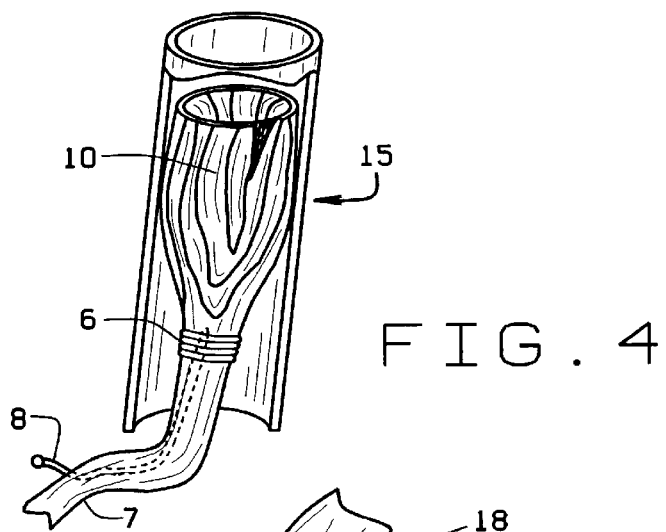
FIG. 4 is a demonstration of the wrapped or folded VAD jacket being passed to its site of endo-pericardial implantation through an appropriate introducer with endoscopic assistance.

FIG. 4 demonstrates the VAD jacket in a wrapped or folded mode, 10, passing through an introducer cannula 15 as would pertain if the device were inserted in an endoscopic procedure. The introducer cannula 15, would ideally be transparent to observe the progress of such a passage, and the remaining items as numbered have been described.

Figure 5:
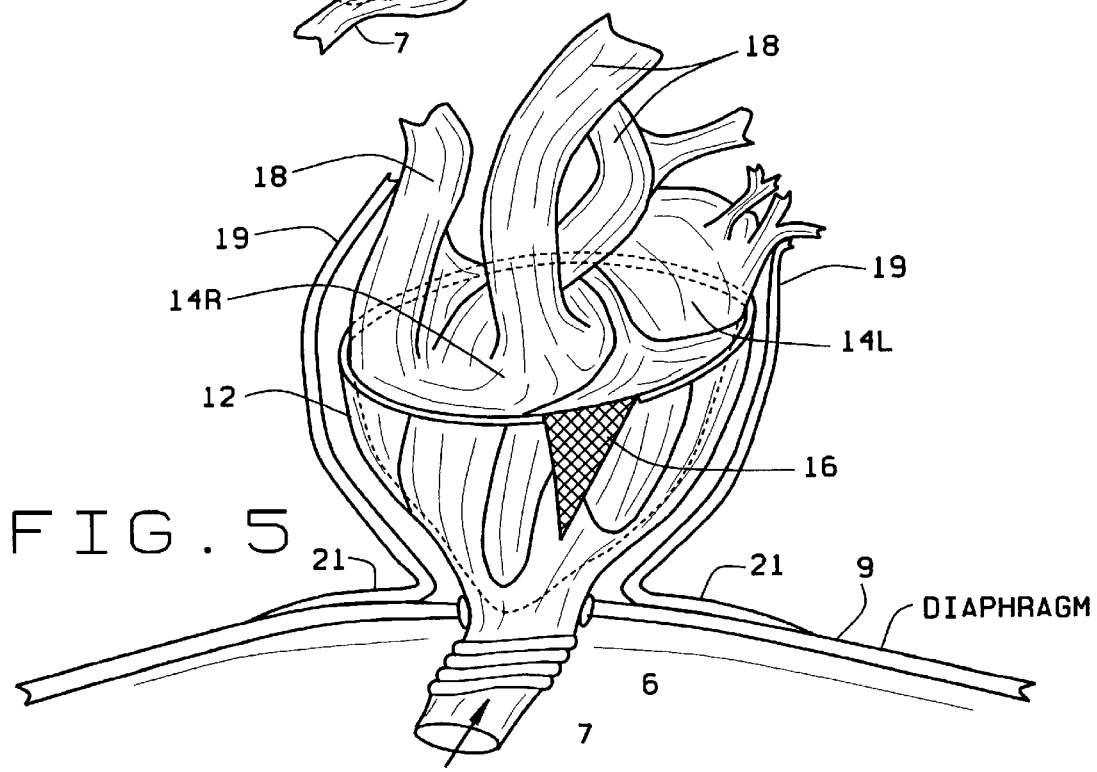
FIG. 5 is another frontal perspective view to show the entire heart and great vessels with the right and left ventricles enveloped by the VAD jacket which in turn is closely fitted within the pericardial sac.

FIG. 5 is an overview of the entire conceptualized viscous cardioplasty jacket application to indicate the congruent cooperative relationship between the ventricular heart masses 14R and 14L, of the VAD itself, and the pericardial sac 19 with the latter's important relationship to the external shell wall of the device. There is also seen the continuation of the pericardial sac upwards to intimately fuse with the outer adventitial layer of the major heart vessels 18 and continuing likewise to descend inferiorly to develop a similarly intimate fusion with the upper surface of the diaphragm 9. The viscous fluid component 15 in the enclosing sac spaces is again shown in its functional state of effective reinforcement of the R14 and L14 ventricular free walls.

What is claimed is:

1. A method of implanting a long term cardiac support device in a pericardial sac for a failing heart, the method including the steps of:
    a) enclosing a heart within the pericardial sac and in which such support device has an outer inelastic ply and in inner elastic lining ply which abuts the ventricular masses of the heart;
    b) instilling a viscous fluid into the device between said inelastic ply and elastic lining ply; and
    c) monitoring the pressure of the viscous fluid in the device.

2. The method of claim 1 wherein said inelastic ply is adjustable to facilitate circumferential fitting of said device to the heart.

3. The method of claim 1 wherein no or minimal pressurization in said device is registered with the result of a viscous cardioplasty reinforcement of the ventricular wall with a resultant reduction in left ventricular and right ventricular diameter and volumes to effect reduction of wall stress thus effectively remodeling of the diastolic and systolic volumetric character of the heart anatomy.

4. The method of claim 1 wherein said viscous fluid is a high viscosity silicone biocompatible liquid.

5. The method of claim 1 wherein said instilling the viscous fluid is a simple gravity fill without any superseding pressure being required.

6. The method of claim 1 wherein minimal pressurization is developed within the device in the range of 2 to 10 mm Hg above the gravity fill at atmospheric pressure.

7. The method of claim 1 wherein the silicone or other viscous fill fluid has a specific gravity of 0.97 or 0.98.

8. The method of claim 1 wherein said device has a diminutive structural dimension such that the pericardial sac can be saved with an ideally congruent fit of the device within the pericardial sac which allows a free choice of closure of the pericardial sac.

9. A method of implanting a long term cardiac support device for a failing heat, the method including:
    a) filling the device from a filling line with any biocompatible polydimethylsilicone or fluoropropylsilicone or equivalent high viscosity fluid of similar density;
    b) a fluid reservoir for said fill fluid; and
    c) implanting said reservoir in the upper abdominal subcutaneous space for refilling of said device.

10. The method of claim 9 wherein the junction of the device and the fluid fill line includes a flexible portion to allow free positioning of the fill line.

11. The method set forth in claim 9 wherein said device may be filled by a syringing flow from an external viscous fluid container and the fill line plugged for revisiting in the subcutaneous site.

12. A method of implanting within the pericardial sac a long term cardiac support device for a failing heart, the method including:
    a) implanting within the pericardial sac a long term cardiac support device having an outer inelastic wall and an inner elastic lining in position to abut the ventricular masses of the heart;
    b) a conduit fill line open to said cardiac support device;
    c) an implantible reservoir having a junction with said conduit fill line;
    d) an adapter syringe for attachment to a fluid reservoir and to said conduit fill line; and
    e) an operable valve in the junction of said flexible reservoir and the fill line for charging fluid from said reservoir to said device.

* * * * *